United States Patent [19]

Kazmaier et al.

[11] Patent Number: 4,792,508
[45] Date of Patent: Dec. 20, 1988

[54] ELECTROPHOTOGRAPHIC PHOTOCONDUCTIVE IMAGING MEMBERS WITH CIS, TRANS PERYLENE ISOMERS

[75] Inventors: Peter M. Kazmaier; Richard A. Burt; Ah-Mee Hor; Cheng-Kuo Hsiao, all of Mississauga, Canada

[73] Assignee: Xerox Corporation, Stamford, Conn.

[21] Appl. No.: 69,544

[22] Filed: Jun. 29, 1987

[51] Int. Cl.⁴ .............................................. G03G 5/14
[52] U.S. Cl. .................................... 430/59; 430/71; 430/76; 430/78; 430/62; 430/96; 546/27
[58] Field of Search .................. 430/58, 59, 78, 71, 430/76; 546/27

[56] References Cited

U.S. PATENT DOCUMENTS

| | | | |
|---|---|---|---|
| 4,156,757 | 5/1979 | Graser et al. | 428/411 |
| 4,429,029 | 7/1984 | Hoffmann et al. | 430/58 |
| 4,514,482 | 4/1985 | Louffy et al. | 430/78 |
| 4,556,622 | 12/1985 | Neumann et al. | 430/58 |
| 4,587,189 | 5/1986 | Ah-Mee Hor et al. | 430/59 |
| 4,714,666 | 12/1987 | Wiedemann et al. | 430/59 |

*Primary Examiner*—J. David Welsh
*Attorney, Agent, or Firm*—E. D. Palallo

[57] ABSTRACT

An improved layered photoresponsive imaging member comprised of a supporting substrate; a photogenerator layer comprised of cis and trans naphthalene imidazole perylene component of the following formula;

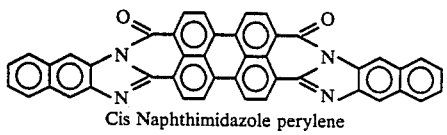

Cis Naphthimidazole perylene

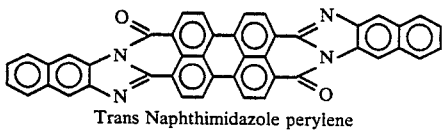

Trans Naphthimidazole perylene and an aryl amine hole transport layer dispersed in a resinous binder.

23 Claims, 2 Drawing Sheets

ELECTROPHOTOGRAPHIC PHOTOCONDUCTIVE IMAGING MEMBERS WITH CIS, TRANS PERYLENE ISOMERS

BACKGROUND OF THE INVENTION

This invention is generally directed to photoresponsive imaging members, and more specifically the present invention is directed to layered photoresponsive members having incorporated therein certain perylene pigment compositions as photogenerating components, and arylamine hole transport layers. Thus, in one embodiment the present invention envisions the selection of specific cis, trans naphthalene perylene pigment compositions as organic photogenerator material components in photoresponsive imaging members containing therein arylamine hole transport molecules. The aforementioned photoresponsive imaging members can be negatively charged when the perylene photogenerating layer is situated between the hole transport layer and the substrate; or positively charged when the hole transport layer is situated between the photogenerating layer and the supporting substrate. Additionally, the photoresponsive imaging members with the perylene pigment compositions as photogenerator substances, and wherein the member further includes therein an aryl amine hole transport layer, are useful in electrophotographic printing and imaging processes, especially xerographic processes wherein negatively charged or positively charged images are rendered visible with developer compositions of the appropriate charge. Of specific importance with respect to the imaging members of the present invention is their utilization in electrophotographic imaging processes wherein diode lasers are selected, since the aforementioned members have sensitivity in the wavelength region extending beyond 720 nanometers, and more specifically possess sensitivity in the range of from about 750 to about 780 nanometers.

Layered photoresponsive imaging members are generally known, reference for example U.S. Pat. No. 4,265,900, the disclosure of which is totally incorporated herein be reference, wherein there is described an imaging member comprised of a photogenerating layer, and an aryl amine hole transport layer. Examples of substances selected for the photogenerating layer of this patent include trigonal selenium, metal phthalocyanines, and metal free phthalocyanines. Additionally, there is described in U.S. Pat. No. 3,121,006, the disclosure of which is totally incorporated herein be reference, a composite xerographic photoconductive member comprised of finely divided particles of a photoconductive inorganic compound dispersed in an electrically insulating organic resin binder. The binder materials disclosed in the U.S. Pat. No. 3,121,006 comprise a material which is incapable of transporting for any significant distance injected charge carriers generated by the photoconductive particles. Accordingly, as a result, the photoconductive particles must be in a substantially contiguous particle-to-particle contact throughout the layer for the purpose of permitting charge dissipation required for a cyclic operation. with a uniform dispersion of photoconductive particles,, a relatively high volume concentration of photoconductor material, about 50 percent by volume, is usually necessary to obtain sufficient photoconductor particle-to-particle contact for rapid discharge. This high photoconductive loading can result in destroying the physical continuity of the resinous binder, thus significantly reducing the mechanical properties thereof. Illustrative examples of specific binder materials disclosed in the U.S. Pat. No. 3,121,006 include polycarbonate resins, polyester resins, polyamide resins, and the like.

Many other patents are in existence describing layered photoresponsive imaging members containing photogenerating substances, such as U.S. Pat. No. 3,041,167, which discloses an overcoated imaging member with a conductive substrate, a photoconductive layer, and an overcoating layer of an electrically insulating polymeric material. This member is utilized in an electrophotographic copying process by, for example, initially charging the member with an electrostatic charge of a first polarity, and imagewise exposing to form an electrostatic latent image which can be subsequently developed to form a visible image. Prior to each succeeding imaging cycle, the imaging member can be charged with an electrostatic charge of a second polarity, which is opposite in polarity to the first polarity. Sufficient additional charges of the second polarity are applied to create across the member a net electrical field of the second polarity. Simultaneously, mobile charges of the first polarity are created in the photoconductive layer such as by applying an electrical potential to the conductive substrate. The imaging potential, which is developed to form the visible image, is present across the photoconductive layer and the overcoating layer.

Photoresponsive imaging members with squaraine photogenerating pigments are also known, reference U.S. Pat. No. 4,415,639, the disclosure of which is totally incorporated herein by reference. In this patent there is illustrated an improved photoresponsive imaging member with a substrate, a hole blocking layer, an optional adhesive interface layer, an organic photogenerating layer, a photoconductive composition capable of enhancing or reducing the intrinsic properties of the photogenerating layer, and an arylamine hole transport layer. As photoconductive compositions for the aforementioned member, there can be selected various squaraine pigments, including hydroxy squaraine compositions. Moreover, there is disclosed in U.S. Pat. No. 3,824,099 certain photosensitive hydroxy squaraine compositions. According to the disclosure of this patent, the squaraine compositions are photosensitive in normal electrostatographic imaging processes.

Photoconductive imaging members containing perylene pigments are also known. There is thus described in Hoechst European Patent Publication No. 0040402, DE3019326, with a filing date of May 21, 1980, N,N'-disubstituted perylene-3,4,9,10-tetracarboxyldiimide pigments as photoconductive substances. Specifically, there is disclosed in this publication evaporated N,N'-bis(3-methoxypropyl)perylene-3,4,9,10-tetracarboxyldiimide dual layered negatively charged photoreceptors with improved spectral response in the wavelength region of 400 to 700 nanometers. A similar disclosure is revealed in Ernst Gunther Schlosser, Journal of Applied Photographic Engineering, Vol. 4, No. 3, page 118 (1978). There is also disclosed in U.S. Pat. No. 3,871,882 photoconductive substances comprised of specific perylene-3,4,9,10-tetracarboxylic acid derivative dyestuffs. In accordance with the teachings of this patent, the photoconductive layer is preferably formed by vapor depositing the dyestuff in a vacuum. Also, there is disclosed in this patent dual layer photoreceptors with perylene-3,4,9,10-tetracarboxylic acid diimide derivatives, which have spectral response in the wavelength region of from 400 to 600 nanometers.

Moreover, there are disclosed in U.S. Pat. No. 4,419,427, electrographic recording mediums with a photosemiconductive double layer comprised of a first layer containing charge carrier perylene diimide producing dyes, and a second layer with one or more compounds which are charge transporting materials when exposed to light, reference the disclosure in column 2, beginning at line 20. Also of interest with respect to this patent is the background information included in columns 1 and 2, wherein perylene dyes of the formula illustrated are presented.

Furthermore, there is presented in copending application U.S. Ser. No. 587,483, entitled Photoconductive Devices Containing Perylene Dye Compositions, the disclosure of which is totally incorporated herein by reference, an ambipolar imaging member comprised of a supporting substrate; a photoconductive layer comprised of specific perylene dyes different than the perylene pigments of the present invention, which dyes are dispersed in a polymeric resinous binder composition; and as a top layer a specific aryl amine hole transporting substance dispersed in an inactive resinous binder. Examples of perylene dyes selected for the photoconductive layer of the copending application include N,N'-di(2,4,6-trimethylphenyl)perylene 3,4,9,10-tetracarboxyldiimide, N,N'-di(2,4,6-trimethoxyphenyl)perylene 3,4,9,10-tetracarboxyldiimide, and N,N'-di(2,6-dimethylphenyl) perylene 3,4,9,10-tetracarboxyldiimide. Additionally, there is disclosed in U.S. Pat. No. 4,429,029 electrophotographic recording members with perylene charge carrier producing dyes, and a charge carrier transporting layer.

In addition, there is illustrated in U.S. Pat. No. 4,587,189, the disclosure of which is totally incorporated herein by reference, photoconductive imaging members with perylene components inclusive of benzimidazole perylenes, which are similar to those of the present invention with the primary exception that they do not contain therein a naphthalene ring structure attached to the nitrogen atoms as more fully illustrated hereinafter. Although the imaging members of the aforementioned patent are useful for their intended purposes, there continues to be a need for highly thermally stable perylenes with spectral response extending into the near infrared. Furthermore, there continues to be a need for perylenes which can be vacuum evaporated to form a contiguous layer which is impervious to organic solvents, such as methylene chloride and the like.

Additionally, there are disclosed in U.S. Pat. No. 4,556,622, photoconductive layers with a halogenated perylene dye sensitizer, reference for example Formulas IV, and IVa, columns 3, and 4. The aforementioned perylenes, for example, do not contain a naphthalene ring structure attached to the nitrogen atom as is the situation with the photogenerating pigments of the present invention; and moreover, this patent does not teach the selection of specific types of arylamines as hole transporting substances thereby enabling rapid transport of charge in the imaging member permitting images of acceptable resolution to be formed for a substantial number of imaging cycles. This patent is of further interest with respect to, for example, the perylene tetracarboxylic acid pigments of Formula III wherein B is a fused on aromatic system, reference German Laid Open Application No. DOS 2314051, see column 2, lines 5 to 12. Accordingly, the aforementioned perylenes are similar to those of the present invention, particularly when B is a phenyl grouping. In U.S. Pat. No. 4,156,757, there are disclosed electrical conductive and semiconductive devices contacting perylene derivatives, of the formulas illustrated in column 1, lines 45 to 52. This reference, however, does not disclose naphthalene perylenes, nor mixtures of certain cis and trans isomers thereof as illustrated herein.

While the above-described photoresponsive imaging members are suitable for their intended purposes, there continues to be a need for improved members, particularly layered members, having incorporated therein specific perylene pigment compositions and aryl amine hole transport compounds. Additionally, there continues to be a need for layered imaging members comprised of specific aryl amine charge transport compositions, and as photogenerating materials naphthalene cis, trans perylene pigments, which members possess sensitivity in a wavelength region exceeding 720 nanometers, have low dark decay characteristics, and high charge acceptance values. Further, these members can be selected for a number of imaging cycles in a xerographic imaging or printing apparatus. Furthermore, there continues to be a need for photoresponsive imaging members which can be positively or negatively charged thus permitting the development of images, including color images, with positively or negatively charged toner compositions. Moreover, there continues to be an important need for disposable imaging members with nontoxic organic pigments. Also, there is a need for disposable imaging members useful in xerographic imaging processes, and xerographic printing systems wherein, for example, light emitting diodes (LED), helium cadmium, or helium neon lasers are selected; and wherein these members are particularly sensitive to the infrared region of the spectrum, that is, from about 720 to about 800 nanometers.

SUMMARY OF THE INVENTION

It is an object of the present invention to provide improved photoresponsive imaging members which are substantially inert to the users thereof.

It is yet another object of the present invention to provide disposable layered photoresponsive imaging members.

A further specific object of the present invention resides in the provision of an improved photoresponsive imaging member with an aryl amine hole transport layer, and a photogenerator layer comprised of specific perylene pigment compositions.

In yet another specific object of the present invention there are provided negatively charged layered photoresponsive imaging members with vacuum evaporated naphthalene cis, trans perylene pigment compositions optionally dispersed in a resinous binder, and thereon a hole transport layer comprised of aryl amine molecules.

There are provided in another object of the present invention positively charged layered photoresponsive imaging members with a top vacuum evaporated naphthalene cis, trans perylene pigment composition optionally dispersed in a resinous binder, and thereunder a hole transport layer comprised of aryl amine molecules.

It is still another object of the present invention to provide improved imaging members sensitive to light in the infrared region of the spectrum, that is from about 750 to about 800 nanometers, enabling their use in xerographic imaging and printing processes wherein diode lasers are selected.

It is yet another object of the present invention to provide imaging and printing methods with the improved photoresponsive imaging members illustrated herein.

These and other objects of the present invention are accomplished by the provision of photoresponsive imaging members having incorporated therein as photogenerating layers hybrid perylenes of the formulas:

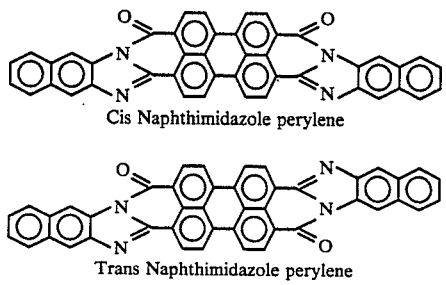

Cis Naphthimidazole perylene

Trans Naphthimidazole perylene with from about 5 to about 95 percent by weight of the cis isomer, and from about 95 to about 5 percent by weight of the trans isomer.

Illustrative specific examples of cis, trans perylene photogenerating pigments useful for incorporation into the imaging members of the present invention include cis and trans naphthimidazole perylenes derived from the reaction of perylene-3,4,9,10-tetracarboxylic anhydride, or its acid with 2,3-diaminonaphthalene; 2,3-diamino-1,4,5,6,7,8-hexafluoronaphthalene; 2,3-diamino-1,4-difluoronaphthalene; 2,3-diamino-1,4-dichloronaphthalene; 2,3-diamino-5,8-dimethylnaphthalene; 2,3-diamino-1,4-dibromonaphthalene; 2,3-diamino-1,4-dicyanonaphthalene; 2,3-diamino-1,4-dimethylnaphthalene; 2,3-diamino-5,8-difluoronaphthalene; 2,3-diamino-5,8-dibromonaphthalene; 2,3-diamino-5,8-dicyanonaphthalene; 2,3-diamino-6,7-difluoronaphthalene; 2,3-diamino-6,7-dichloronaphthalene; 2,3-diamino-6,7-dicyanonaphthalene; 2,3-diamino-5,8-dichloronaphthalene; 2,3-diamino-6,7-dimethylnaphthalene; 2,3-diamino-1,4,5,6,7,8-hexachloronaphthalene; 2,3-diamino-1,4,5,6,7,8-hexabromonaphthalene; or 2,3-diamino-6,7-dibromonaphthalene; and wherein the product mixture contains from about 5 to about 95 percent by weight of the cis isomer, and from about 95 to about 5 percent by weight of the trans isomer.

The perylene compositions illustrated herein are generally prepared by the condensation reaction of perylene-3,4,9,10-tetracarboxylic acid; or the corresponding anhydrides with an appropriate diaminonaphthalene in quinoline, or 1-chloronaphthalene in the presence of a catalyst, and with heating at elevated temperatures of, for example, from about 180° C. to about 230° C., the details of which are described in German Patent Publications Nos. 2,451,780; 2,451,781; 2,451,782; 2,451,783; 2,451,784; 3,016,765; French Pat. No. 7723888; British Patent Publication Nos. 857,130; 901,694; 1,095,196; and Heinz Langhals and Sabine Grundner in Chemische Berichte 119, 2373-2376 (1986), the disclosure of each of the aforementioned publications and patents being totally incorporated herein by reference.

In one specific process embodiment, the perylene pigment s of the present invention can be prepared by the condensation reaction of perylene-3,4,9,10-tetracarboxylic acid, or its corresponding anhydrides with an amine in a molar ratio of from about 1:2 to about 1:10, and preferably in a ratio of from about 1:2 to about 1:3. This reaction is generally accomplished at a temperature of from about 180° C. to about 260° C., and preferably at a temperature of about 250° C. with stirring and without a catalyst. Subsequently, the desired product is isolated from the reaction mixture by known techniques such as filtration. Examples of first reactants include pyrylene-3,4,9,10-tetracarboxylic acid, perylene-3,4,9,10-tetracarboxylic acid dianhydride, and the like. Illustrative amine reactants include those as recited herein such as 2,3-diaminonaphthalene; 2,3-diamino-1,4,5,6,7,8-hexafluoronaphthalene; 2,3-diamino-1,4-difluoronaphthalene; 2,3-diamino-1,4-dichloronaphthalene; 2,3-diamino-5,8-dimethylnaphthalene; 2,3-diamino-1,4-dibromonaphthalene; 2,3-diamino-1,4-dicyanonaphthalene; 2,3-diamino-1,4-dimethylnaphthalene; 2,3-diamino-5,8-difluoronaphthalene; 2,3-diamino-5,8-dibromonaphthalene; 2,3-diamino-5,8-dicyanonaphthalene; 2,3-diamino-6,7-difluoronaphthalene; 2,3-diamino-6,7-dichloronaphthalene; 2,3-diamino-6,7-dicyanonaphthalene; 2,3-diamino-5,8-dichloronaphthalene; 2,3-diamino-6,7-dimethylnaphthalene; 2,3-diamino-1,4,5,6,7,8-hexachloronaphthalene; 2,3-diamino-1,4,5,6,7,8-hexabromonaphthalene; or 2,3-diamino-6,7-dibromonaphthalene With further respect to the process for preparing the cis, trans perylene mixtures of the present invention, they are generally formed concomitantly, and wherein the cis, trans ratio varies from about 0.43 to about 2.33. Additionally, when catalysts are selected for the reaction, reference the aforementioned German, British and French publications, there is utilized in effective amounts components such as anhydrous zinc chloride, anhydrous zinc acetate, zinc oxide, acetic acid, hydrochloric acid, and the like.

Numerous different layered photoresponsive imaging members with the perylene pigments illustrated herein can be fabricated. In one embodiment, thus the layered photoresponsive imaging members are comprised of a supporting substrate, an aryl amine hole transport layer, and situated therebetween a vacuum evaporated photogenerator layer comprised of the cis, trans perylene pigments illustrated herein. Another embodiment of the present invention is directed to positively charged layered photoresponsive imaging members comprised of a supporting substrate, an aryl amine hole transport layer, and as a top overcoating a vacuum evaporated photogenerator layer comprised of the perylene pigments illustrated hereinbefore. Moreover, there is provided in accordance with the present invention an improved negatively charged photoresponsive imaging member comprised of a supporting substrate, a thin adhesive layer, a photogenerator vacuum evaporated layer comprised of the perylene pigments illustrated herein optionally dispersed in a polymeric resinous binder, and as a top layer aryl amine hole transporting molecules dispersed in a polymeric resinous binder.

The improved photoresponsive imaging members of the present invention can be prepared by a number of methods, the process parameters and the order of coating of the layers being dependent on the member desired. Thus, for example, these imaging members are prepared by vacuum deposition of the photogenerator layer of a supporting substrate with an adhesive layer thereon, and subsequently depositing by solution coating the hole transport layer. The imaging members suitable for positive charging can be prepared by reversing the order of deposition of photogenerator and hole transport layers.

Imaging members having incorporated therein the cis, trans naphthalene perylene photogenerating pigments of the present invention are useful in various electrophotographic imaging systems, particularly those conventionally known as xerographic processes. Specifically, the imaging members of the present invention can be selected for xerographic imaging and printing processes wherein the perylene pigments absorb light of a wavelength in excess of 720 nanometers, and more specifically from about 720 nanometers to about 780 nanometers. In these processes, electrostatic latent images are initially formed on the imaging member followed by development, and thereafter transferring the image to a suitable substrate.

BRIEF DESCRIPTION OF THE DRAWINGS

For a better understanding of the present invention and further features thereof, reference is made to the following detailed description of various preferred embodiments wherein.

DESCRIPTION OF THE PREFERRED EMBODIMENTS

Figure 1:
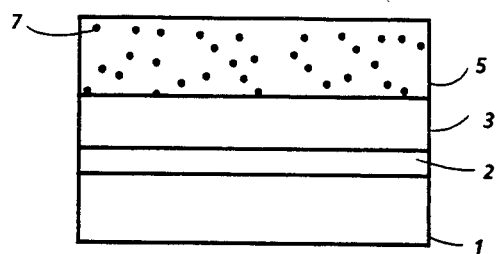
FIG. 1 is a partially schematic cross-sectional view of a photoresponsive imaging member of the present invention.

Illustrated in FIG. 1 is a photoresponsive imaging member of the present invention comprised of a substrate 1, an adhesive layer 2, a photogenerator layer 3 comprised of a mixture of the cis and trans isomers as illustrated hereinbefore, wherein the cis isomer is present in an amount of from about 30 to 70 percent, and the trans isomer is present in an amount of from 30 to 70 percent; and a charge transport layer 5 comprised of N,N'-diphenyl-N,N'-bis(3-methylphenyl)-1,1'-biphenyl-4,4'-diamine dispersed in a polycarbonate resinous binder 7.

Figure 2:
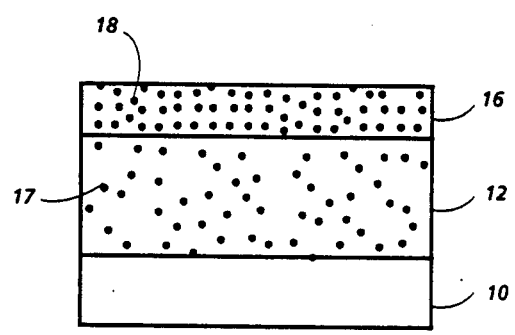
FIG. 2 is a partially schematic cross-sectional view of a photoresponsive imaging member of the present invention.

Illustrated in FIG. 2 is a positively charged photoresponsive imaging member of the present invention comprised of a supporting substrate 10, a charge transport layer 12 comprised of N,N'-diphenyl-N,N'-bis(3-methylphenyl)-1,1'-biphenyl-4,4'-diamine dispersed in a polycarbonate resinous binder 17 with 55 percent by weight of the arylamine; and a photogenerator layer 16 comprised of a mixture of the cis and trans isomers as illustrated with reference to FIG. 1, which isomers are dispersed in an inactive resinous binder 18.

Substrate layers selected for the imaging members of the present invention can be opaque or substantially transparent, and may comprise any suitable material having the requisite mechanical properties. Thus, the substrate may comprise a layer of insulating material including inorganic or organic polymeric materials, such as Mylar a commercially available polymer; a layer of an organic or inorganic material with a semiconductive surface layer such as indium tin oxide, or aluminum arranged thereon; or a conductive material inclusive of aluminum, chromium, nickel, brass, or the like. The substrate may be flexible or rigid and may have a number of many different configurations, such as, for example a plate, a cylindrical drum, a scroll, an endless flexible belt, and the like. Preferably, the substrate is in the form of a seamless flexible belt. In some situations, it may be desirable to coat on the back of the substrate, particularly when the substrate is a flexible organic polymeric material, an anticurl layer, such as for example polycarbonate materials commercially available as Makrolon ®.

The thickness of the substrate layer depends on many factors, including economical considerations, thus this layer may be of substantial thickness, for example or 2,500 microns; or of minimum thickness providing there are no adverse effects on the system. In one preferred embodiment, the thickness of this layer is from about 75 microns to about 250 microns.

With further regard to the imaging members of the present invention, the photogenerator layer is preferably comprised of 100 percent of the cis, trans perylene pigments disclosed herein. However, providing the objectives of the present invention are achieved, these perylene pigments can be dispersed in resinous binders. Generally, the thickness of the perylene photogenerator layer depends on a number of considerations including the thicknesses of the other layers, and the percentage of the photogenerator material present. Accordingly, this layer can be of a thickness of from about 0.05 micron to about 10 microns when the photogenerator perylene composition is present in an amount of from about 5 percent to about 100 percent by volume. Preferably, this layer is of a thickness of from about 0.25 micron to about 1 micron, when the photogenerator cis, trans perylene composition is present in an amount of 30 percent by volume. In one very specific preferred embodiment, the vacuum deposited photogenerating layers are of a thickness of from about 0.07 micron to about 0.5 micron. The maximum thickness of this layer is dependent primarily upon factors such as photosensitivity, electrical properties, and mechanical considerations.

Illustrative examples of polymeric binder resinous materials that can be selected for the cis, trans photogenerator pigment include those polymers as disclosed in U.S. Pat. No. 3,121,006, the disclosure of which is totally incorporated herein by reference. Specific examples of binders include polyesters, polyvinyl butyral, Formvar ®, polycarbonate resins, polyvinyl carbazole, epoxy resins, phenoxy resins, especially the commercially available poly(hydroxyether) resins, and the like.

As adhesive layers generally of a thickness of from about 0.05 micron to 1 micron, there can be selected various known substances inclusive of polyesters such as those commercially available from E. I. DuPont as 49,000 polyesters. In addition, there can be included in the photoresponsive imaging members of the present invention other layers such as silane interfacial layers in thicknesses of less than about one micron and greater than about 0.05 micron.

Aryl amines selected for the hole transporting layer, which layer generally is of a thickness of from about 5 microns to about 50 microns, and preferably of a thickness of from about 10 microns to about 40 microns, include those of the following formula:

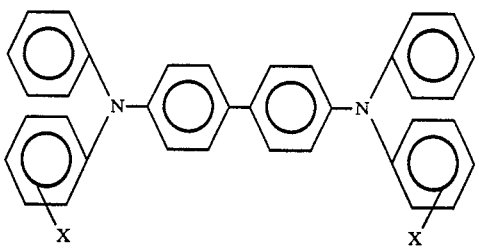

dispersed in a highly insulating and transparent organic resinous binder wherein X is an alkyl group or a halogen, especially those substituents selected from the group consisting of (ortho) $CH_3$, (para) $CH_3$, (ortho) Cl, (meta) Cl, and (para) Cl.

Examples of specific arylamines include N,N'-diphenyl-N,N'-bis(alkylphenyl-1,1-biphenyl-4,4'-diamine wherein alkyl is selected from the group consisting of methyl, such as 2-methyl, 3-methyl and 4-methyl, ethyl, propyl, butyl, hexyl, and the like; and N,N'-diphenyl-N,N'-bis(halo phenyl)-1,1'-biphenyl-4,4'-diamine wherein halo is preferably 2-chloro, 3-chloro or 4-chloro.

Examples of the highly insulating and transparent resinous material or inactive binder resinous material for the transport layers include materials such as those described in U.S. Pat. No. 3,121,006, the disclosure of which is totally incorporated herein by reference. Specific examples of organic resinous materials include polycarbonates, acrylate polymers, vinyl polymers, cellulose polymers, polyesters, polysiloxanes, polyamides, polyurethanes and epoxies as well as block, random or alternating copolymers thereof. Preferred electrically inactive binders are comprised of polycarbonate resins having a molecular weight of from about 20,000 to about 100,000 with a molecular weight of from about 50,000 to about 100,000 being particularly preferred. Generally, the resinous binder contains from about 10 to abut 75 percent by weight of the active material corresponding to the foregoing formula, and preferably from about 35 percent to about 50 percent of this material.

Also included within the scope of the present invention are methods of printing and imaging with the photoconductive imaging members illustrated herein. These methods generally involve the formation of an electrostatic latent image on the imaging member, followed by developing the image with a toner composition, subsequently transferring the image to a suitable substrate, and permanently affixing the image thereto. In those environments wherein the device is to be used in a printing mode, the imaging method involves the same steps with the exception that the exposure step can be accomplished with a laser device or image bar. Examples of toner compositions that can be selected include those comprised of resin particles, pigment particles, charge enhancing additive components, and other additives, reference for example U.S. Pat. Nos. 4,560,635; 4,469,770; 4,490,455; and 4,298,672, the disclosures of each of these patents being totally incorporated herein by reference. Usually development is accomplished with a developer comprised of toner compositions and carrier components, which are illustrated in the aforementioned patents, particularly the U.S. Pat. No. 4,298,672.

The invention will now be described in detail with reference to specific preferred embodiments thereof, it being understood that these examples are intended to be illustrative only. Also, this invention is not intended to be limited to the materials, conditions or process parameters recited herein, it being noted that all parts and percentages are by weight unless otherwise indicated.

EXAMPLE I

Synthesis of Cis, Trans Naphthimidazole Perylene:

A 500 milliliter 3-necked round-bottomed flask equipped with a mechanical stirrer, thermometer, Dean Stark trap topped with a nitrogen inlet was charged with perylene tetracarboxylic acid anhydride (9.80 grams), and 2,3-diaminonaphthalene (19.7 grams and 1-chloronaphthalene) (150 milliliters). The reaction mixture was heated at 250° C. for 20 hours after which the product was isolated by filtration. Purification was accomplished by boiling with acetone for thirty minutes, followed by heating with fresh 1-chloronaphthalene for 17 hours at 258° C. On isolation and washing with diethyl ether, the yield of product was about 90 percent.

The resulting product was further purified by heating to 540° C. in an evacuated tube in a stream of nitrogen, followed by collecting the sublimate. This material was then used for the electrical evaluation.

The product, which was comprised of the cis naphthimidazole perylene, 40 percent by weight, and the trans naphthimidazole perylene, 60 percent by weight, of the formulas as illustrated herein, was characterized by combustion analysis.

| Calculated: | Found: |
| --- | --- |
| C: 83.01 | C: 82.93 |
| H: 3.17 | H: 3.14 |
| N: 8.80 | N: 8.80 |

The solution absorption spectrum evidenced absorption maxima at 648 and 598 nanometers. The solid state absorption of naphthimidazole perylene particles in poly(vinyl acetate) evidenced maxima at about 555 and 710 nanometers. Also, the infrared spectra indicated strong characteristic perylene imidazole absorptions at 1684, 1599 and 1588 wave numbers.

EXAMPLE II

A photoresponsive imaging member was prepared by providing an aluminized Mylar substrate in a thickness of 75 microns with a silane interfacial layer (gamma-(amino propyl) methyl diethoxysilane), 0.05 micron in thickness thereover, a polyester, available from E. I. DuPont as 49,000 polyester, adhesive layer thereon in a thickness of 0.05 micron; and depositing thereover with a Varian Model 3117 vacuum coater a photogenerating layer of the naphthimidazole perylene obtained by the process of Example I. This layer had a final thickness of 0.1 micron. More specifically, the photogenerator component was heated in a tantalum boat to about 350° C., and the vacuum coater evacuated to a pressure of about $10^{-5}$ Torr. Also the substrate was mounted 16 centimeters from the boat, and the photogenerator layer was deposited at a rate of about 0.5 Angstroms/second.

Thereafter, the above photogenerating layer was overcoated with an amine charge transport layer prepared as follows:

A transport layer with 65 percent by weight Merlon ®, a polycarbonate resin, was mixed with 35 percent by weight N,N'-diphenyl-N,N'-bis(3-methylphenyl)-1,1'-biphenyl-4,4'-diamine, and 7 percent by weight in methylene chloride in an amber bottle. The resulting mixture was then coated in a dry thickness of 15 microns on top of the above photogenerating layer using a multiple clearance film applicator (10 mils wet gap thickness). The resulting member was then dried in a forced air oven at 135° C. for 20 minutes.

Figure 3:
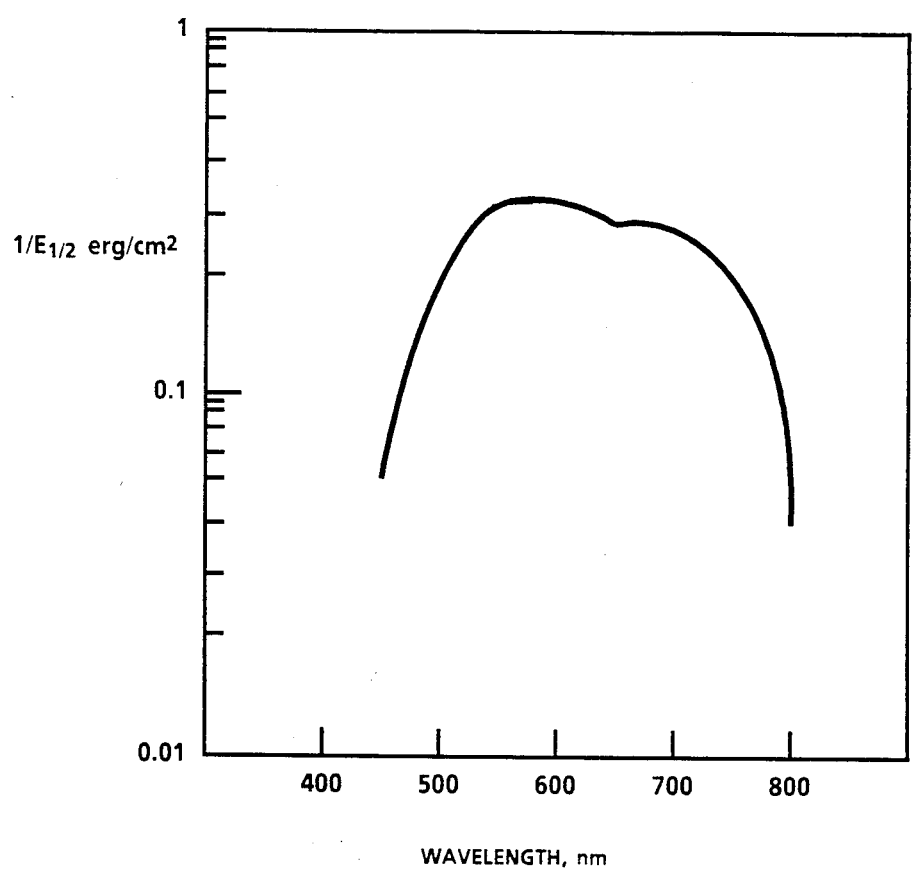
FIG. 3 represents a line graph wherein there is plotted the $E_{\frac{1}{2}}$ value and wavelength in nanometers for the photoresponsive imaging member of Example II.

The photosensitivity of the aforementioned imaging member, reference FIG. 3, was then determined by electrostatically charging the surface thereof with a corona discharge source until the surface potential, as measured by a capacitively coupled probe attached to an electrometer, attained an initial dark value $V_O$ of $-800$ volts. The front surface of the charged member was then exposed to light from a filtered Xenon lamp, XBO 75 watt source, allowing light in the wavelength range 720 to 780 nanometers to reach the members surface, which exposure causing reduction of the surface potential to half its initial value, $E_\frac{1}{2}$, and the percent discharge of surface potential due to various exposure energies was then determined. The photosensitivity can be determined in terms of the exposure in ergs/cm² necessary to discharge the member from the initial surface potential to half that value. The higher the photosensitivity, the smaller the exposure energy required to discharge the layer to 50 percent of the surface potential. With white light 400 to 800 nanometers exposure, the $E_\frac{1}{2}$ value for this member was found to be 6.7 erg/cm², and the percent discharge at an exposure level of 10 erg/cm² was 67 percent.

Similar photoresponsive imaging members can be prepared by repeating the above procedure including wherein, for example, as interfacial layers there can be selected the components described in U.S. Pat. Nos. 4,291,110; 4,338,387; and 4,286,033, the disclosures of which are totally incorporated herein by reference.

Other modifications of the present invention may occur to those skilled in the art based upon a review of the present disclosure, and these modifications, including equivalents thereof, are intended to be included within the scope of the present invention.

What is claimed is:

1. An improved layered photoresponsive imaging member comprised of a supporting substrate; a photogenerator layer comprised of cis and trans naphthalene imidazole perylene component of the following formula;

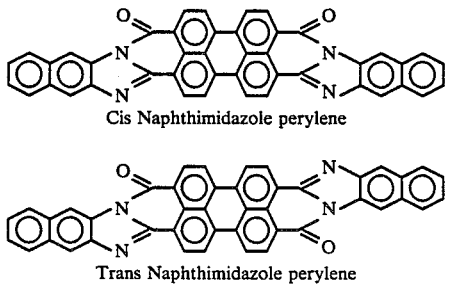

Cis Naphthimidazole perylene

Trans Naphthimidazole perylene and an aryl amine hole transport layer dispersed in a resinous binder.

2. An imaging member in accordance with claim 1 wherein the supporting substrate is comprised of a conductive metallic substance, or an insulating polymeric composition overcoated with an electrically conductive layer.

3. An imaging member in accordance with claim 1 wherein the supporting substrate is aluminum.

4. An imaging member in accordance with claim 1 wherein the supporting substrate is overcoated with a polymeric adhesive layer.

5. An imaging member in accordance with claim 4 wherein the adhesive layer is a polyester resin.

6. An imaging member in accordance with claim 4 further including an interfacial silane layer.

7. An imaging member in accordance with claim 1 wherein the aryl amine charge transporting layer comprises molecules of the formula:

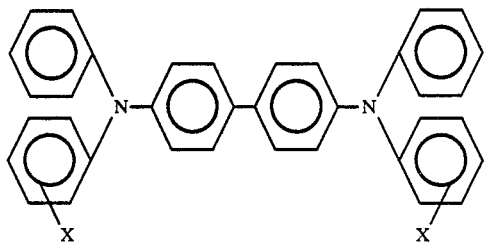

dispersed in a resinous binder and wherein X is selected from the group consisting of halogen and alkyl.

8. An imaging member in accordance with claim 7 wherein X is selected from (ortho) $CH_3$, (meta) $CH_3$, (para) $CH_3$, (ortho) Cl, (meta) Cl, and (para) Cl.

9. An imaging member in accordance with claim 1 wherein the aryl amine is N,N'-diphenyl-N,N'-bis(3-methylphenyl)-1,1'-biphenyl-4,4'-diamine.

10. An imaging member in accordance with claim 1 wherein the resinous binder is a polycarbonate or polyvinyl carbazole.

11. An imaging member in accordance with claim 1 wherein the perylene pigments are dispersed in a resinous binder in an amount of from about 5 percent to about 95 percent by volume, and the aryl amine hole transport molecules are dispersed in a resinous binder in an amount of from about 10 to about 75 percent by weight.

12. An imaging member in accordance with claim 11 wherein the resinous binder for the perylene pigments is a polyester, a polyvinyl carbazole, a polyvinyl butyral, a polycarbonate, or a phenoxy resin.

13. An imaging member in accordance with claim 1 wherein the aryl amine hole transport layer is situated between the supporting substrate and the photogenerating layer.

14. An imaging member in accordance with claim 1 wherein the cis isomer is present in an amount of from about 30 percent to about 70 percent.

15. An imaging member in accordance with claim 1 wherein the trans isomer is present in an amount of from 30 percent about to about 70 percent.

16. An imaging member in accordance with claim 15 wherein the supporting substrate is comprised of a conductive metallic substance, or an insulating polymeric composition overcoated with an electrically conductive layer.

17. An imaging member in accordance with claim 15 wherein the supporting substrate is aluminum.

18. An imaging member in accordance with claim 16 wherein the supporting conductive substrate is overcoated with a thin polymeric adhesive layer.

19. A method of imaging which comprises forming an electrostatic latent image on the imaging member of claim 1 causing development thereof with a toner composition; subsequently transferring the developed image to a suitable substrate; and permanently affixing the image thereto.

20. A method of imaging in accordance with claim 19 wherein the member is sensitive at a wavelength region of from about 450 to about 780 nanometers.

21. A method of imaging in accordance with claim 19 wherein the imaging member contains a photogenerating pigment from with about 30 to 70 percent of the cis naphthalene imidazole, and from about 70 to about 30 percent by weight of the trans naphthalene imidazole of the formula of claim 1.

22. An imaging member in accordance with claim 1 with photosensitivity in a wavelength region of from about 450 to about 800 nanometers.

23. An imaging member in accordance with claim 1 wherein the photogenerating layer is formulated by the vacuum deposition on the supporting substrate.

* * * * *